United States Patent [19]
Sanford et al.

[11] Patent Number: 5,478,744
[45] Date of Patent: Dec. 26, 1995

[54] METHOD FOR TRANSPORTING SUBSTANCES INTO LIVING CELLS AND TISSUES AND APPARATUS THEREFOR

[75] Inventors: John C. Sanford, Geneva; Edward D. Wolf, Ithaca; Nelson K. Allen, Newfield, all of N.Y.

[73] Assignee: Cornell Research Foundation, Inc., Ithaca, N.Y.

[21] Appl. No.: 289,206

[22] Filed: Aug. 12, 1994

Related U.S. Application Data

[62] Division of Ser. No. 637,954, Jan. 9, 1991, Pat. No. 5,371,015, which is a continuation of Ser. No. 74,652, Jul. 17, 1987, abandoned, which is a division of Ser. No. 670,771, Nov. 13, 1984, Pat. No. 4,945,050.

[51] Int. Cl.⁶ ............................................. C12M 1/00
[52] U.S. Cl. .................... 435/285.1; 435/285.3; 435/283.1; 935/85
[58] Field of Search ................................ 435/287, 313; 935/85; 604/68, 70, 72, 140, 146, 147; 222/630, 399; 239/409

[56] References Cited

U.S. PATENT DOCUMENTS

| | | | |
|---|---|---|---|
| 2,605,763 | 8/1952 | Smoot | 604/70 |
| 2,764,977 | 10/1956 | Ferguson | 604/70 |
| 3,130,575 | 4/1964 | Rogers | 73/12 |
| 3,343,400 | 9/1967 | Rogers et al. | 73/12 |
| 3,404,599 | 10/1968 | Annis | 73/12 |
| 3,515,130 | 6/1970 | Tsujino . | |
| 3,688,765 | 9/1972 | Gasaway | 604/70 |
| 3,782,380 | 1/1974 | Van Dor Gaast | 604/68 |
| 3,802,430 | 4/1974 | Schwebel et al. | 604/69 |
| 3,837,284 | 9/1974 | Waldersen | 604/130 X |
| 4,174,068 | 11/1979 | Rudolph | 222/630 |
| 4,326,524 | 4/1982 | Drake, Jr. et al. | 605/130 X |
| 4,358,302 | 11/1982 | Dahneke | 239/424 |
| 4,421,508 | 12/1983 | Cohen | 604/70 |
| 4,473,328 | 9/1984 | Hengesbach | 222/630 |
| 4,573,801 | 3/1986 | Leschonski et al. | 222/630 |
| 4,945,050 | 7/1990 | Sanford et al. | 435/172.1 |
| 5,036,006 | 7/1991 | Sanford et al. | 435/172.3 |
| 5,100,792 | 3/1992 | Sanford et al. | 435/172.1 |

FOREIGN PATENT DOCUMENTS 568237  3/1945  United Kingdom .

OTHER PUBLICATIONS

Lachopelle et al. "Tatouages Permanents Consécutifs a des Injections por Dermo–Jet" Am. Dermatol. Venereal. vol. 109 (1982) pp. 939–946.

*Primary Examiner*—William H. Beisner
*Attorney, Agent, or Firm*—Sughrue, Mion, Zinn, Macpeak & Seas

[57] ABSTRACT

Inert or biologically active particles are propelled at cell at a speed whereby the particles penetrate the surface of the cells and become incorporated into the interior of the cells. The process can be used to mark cells or tissue or to biochemically affect tissues or tissue in situ as well as single cells in vitro. Apparatus for propelling the particles toward target cells or tissues are also disclosed. A method for releasing particles adhered to a rotor device is also disclosed.

2 Claims, 10 Drawing Sheets

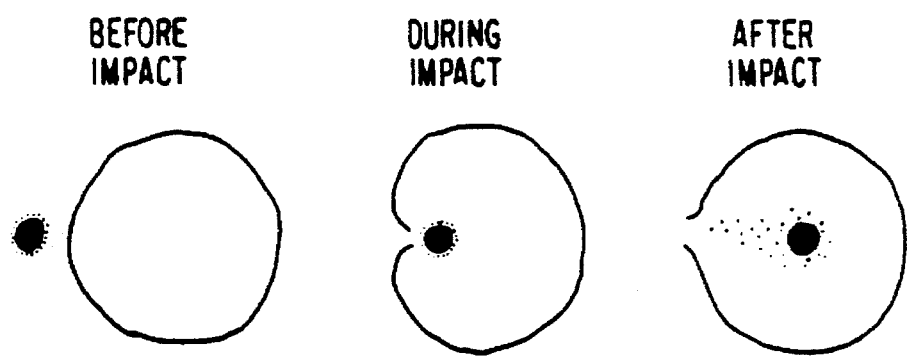
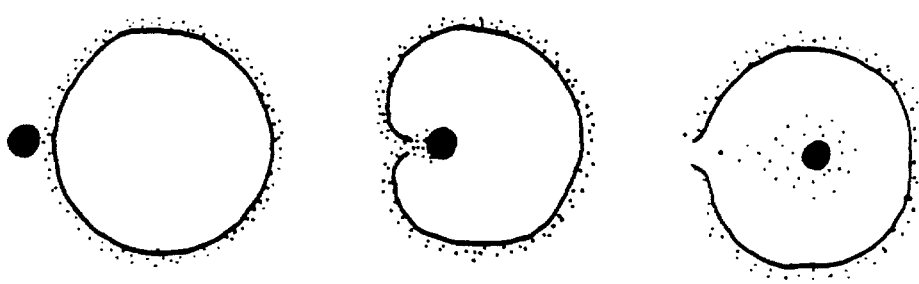
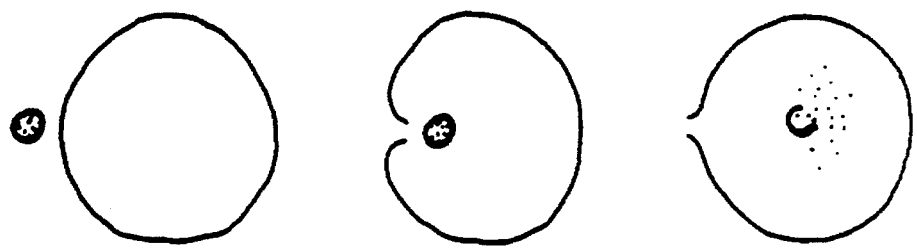
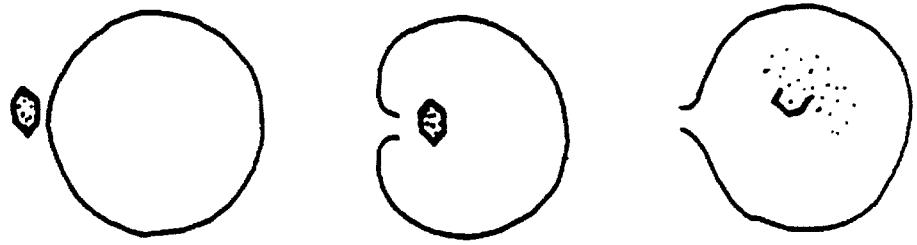
= BIOLOGICALLY ACTIVE SUBSTANCES 5,478,744

METHOD FOR TRANSPORTING SUBSTANCES INTO LIVING CELLS AND TISSUES AND APPARATUS THEREFOR

This is a divisional of application Ser. No. 07/637,954 filed Jan. 9, 1991, now U.S. Pat. No. 5,371,015, which is a continuation of application Ser. No. 07/074,652, filed Jul. 17, 1987 (abandoned), which is a divisional of Ser. No. 06/670,771, filed Nov. 13, 1984, now U.S. Pat. No. 4,945,050.

The present invention relates to a novel method and apparatus for transporting, substances into living cells and tissues without killing the cells and tissues.

BACKGROUND OF THE INVENTION

Biologists often need to introduce into living cells a wide range of substances which are normally excluded from the cell by cell walls and outer cell membranes. Such substances include biological stains, proteins, nucleic acids, organelles, chromosomes, and nuclei.

The importance of introducing biological substances into cells is reflected by the large amount of work which has been done in this area, and the expensive technologies which have been developed to achieve this end. While diverse applications of biological delivery systems are known (*Introduction of Macromolecules into Viable Mammalian Cells,* (Ed. R. Baserga, C. Crose, G. Rovera), Winstar Symposium Series VI, 1980, A.R. Liss Inc., New York), one application of central importance will clearly be the introduction of genetic material into cells for the purpose of genetic engineering. Existing technologies for transporting genetic material into living cells involve uptake mechanisms, fusion mechanisms, and microinjection mechanisms.

Uptake mechanisms include: (a) induction of enhanced membrane permeability by use of $Ca^{++}$ and temperature shock (Mandel, M. and Higa, A., 1970, "Calcium Dependent Bacteriophage DNA Infection," *J. Mol. Biol.,* 53: 159–162; Dityatkin, S. Y., Lisovskaya, K. V., Panzhava, N. N., Iliashenko, B. N., 1972, "Frozen-thawed Bacteria as Recipients of Isolated Coliphage DNA", *Biochimica et Biophysica Acta,* 281: 319–323); (b) use of surface binding agents such as polyethylene glycol (PEG) (Chang, S. and Cohen, S. N., 1979, "High Frequency Transformation of *Bacillus subtilis* Protoplasts by Plasmid DNA", *Mol. Gen. Genet.,* 168: 111–115; Krens, F. A., Molendijk, L., Wullens, G. J., and Schilperoort, R. A., 1982, "In vitro Transformation of Plant Protoplasts with Ti-Plasmid DNA", *Nature,* 296: 72), or $Ca(PO_4)_2$ (Graham, F. L., and van der Eb, A. J., 1973, "A New Technique for the Assay of Infectivity of Human Adenovirus 5 DNA", *Virology,* 52: 456; Wigler, M., Sweet, R., Sim, G. K., Wold, B., Pellicer, A., Lacey, E., Maniatis, T., Silverstein, S., and Axel, R., 1979, "Transformation of Mammalian Cells with Genes from Procaryotes and Eucaryotes", *Cell* 16: 777); and (c) phagocytosis of particles such as liposomes (Uchimiya, H., Ohgawara, T., and Harada, H., 1982, "Liposome-mediated Transfer of Plasmid DNA into Plant Protoplasts", In: Fujiwara A. (ed.), *Proc. 5th Intl. Cong. Plant Tissue and Cell Culture,* Jap. Assoc. for Plant Tissue Culture, Tokyo, pp. 507–508), organelles (Potrykus I., 1973, "Transplantation of Chloroplasts into Protoplasts of Petunia", *Z. Pflanzenphysiol.,* 70: 364–366), or bacteria (Cocking, E. C., 1972, "Plant Cell Protoplasts Isolation and Development", *Ann. Rev. Plant Physiol.,* 23: 29–50), into the cell. These uptake mechanisms generally involve suspensions of single cells, from which any existing cell wall materials have been removed enzymatically.

Uptake protocols are generally quite simple, and allow treatment of large numbers of cells en masse. However, such methods tend to have very low efficiency. In plant protoplasts, transformation frequencies tend to be one in 10,000 or less, while in animal cell uptake systems, transformation frequencies tend to be even lower. In such systems most cells are unaffected, and special cell selection procedures are required to recover the rare cells which have been transformed (Power, J. B. and Cocking, E. G., 1977, "Selection Systems for Somatic Hybrids", In: Reinert, J. and Bajaj, Y. P. S. (eds.) *Plant Cell, Tissue, and Organ Culture,* Springer-Verlag, N.Y., pp. 497–505).

Fusion mechanisms incorporate new genetic material into a cell by allowing one cell to fuse with another cell. A variation on this procedure involves "ghost" cells. The membrane of killed cells are allowed to fill with a given DNA solution, such that cell fusion incorporates the DNA from the carrier "cell" into the living cell. Cell-to-cell fusion can be induced with the aid of substances such as PEG (Bajaj, Y. P. S., 1982, "Protoplast Isolation, Culture and Somatic Hybridization", In: Reinert, J. and Bajaj, Y. P. S. (eds.) *Plant Cell, Tissue, and Organ Culture,* Springer-Verlag, N.Y. pp. 467–496), and Sendai virus particles (Uchida, T., Yamaizumi, M., Mekada, E., Okada, Y., 1980, "Methods Using HVJ (Sendai Virus) for Introducing Substances into Mammalian Cells", In: *Introduction of Macromolecules into Viable Mammalian Cells,* Windsor Symposium Series V.I. A.R. Liss Inc., N.Y., pp. 169–185).

As with uptake mechanisms, fusion technologies rely upon the use of single cell suspensions, where cells are enzymatically stripped of any cell wall material. While fusion technologies can have relatively good efficiencies in terms of numbers of cells affected, the problems of cell selection can be more complex, and the resulting cells are typically of elevated ploidy, which can limit their usefulness.

Microinjection technologies employ extremely fine, drawn out capillary tubes, which are sometimes called micropipettes. These capillary tubes can be made sufficiently small to be used as syringe needles for the direct injection of biological substances into certain types of individual cells (Diacumakos, E. G., 1973, "Methods for Microinjection of Human Somatic Cells in Culture", In: Prescott DM (ed.) *Methods in Cell Biology,* Academic Press, N.Y. pp. 287–311; Graessmann, M. and Graessman, A., 1983, "Microinjection of Tissue Culture Cells", *Methods in Enzymology,* 101: 482–492). When small cells need to be injected, very sharp microelectrodes are required, whose tips are very easily broken or clogged. Very high pressures are required to cause bulk flow through orifices smaller than one micron. Regulation of such bulk flow is very difficult. The entire process is something of an art, requiring different modifications for different cell types. One modification of microinjection involves pricking with a solid-glass drawn needle, which carries in biological solutions which are bathing the cell (Yamamoto, F., Furusawa, M., Furusawa, I., and Obinata, M., 1982, "The "Pricking" Method", *Exp. Cell Res.,* 142: 79–84). Another modification, called ionophoresis (Purres, R. D., 1981, *Microelectrode Methods for Intracellular Recording and Ionophoresis,* Academic Press, N.Y., p. 146; Ocho, M., Nakai, S., Tasaka, K., Watanabe, S., and Oda, T., 1981, "Micro-injection of Nucleic Acids Into Cultured Mammalian Cells by Electrophoresis", *Acta Med. Okayama,* 35(5): 381–384), uses electrophoresis of substances out of the microelectrode and into the cell, as an alternative to high pressure bulk flow.

Microinjection procedures can give extremely high efficiencies relative to delivery into the cell. Because of this, microinjection has been used successfully in the transformation of individual egg cells. One disadvantage of microinjection is that it requires single cell manipulations and is therefore inappropriate for treating masses of cells and is generally a very tedious and difficult technology. Microinjection is a technology which would not be easily universalized or automated.

While a variety of biological delivery systems presently exist, none of these technologies is free from major limitations. Perhaps the greatest single limitation of all of these technologies is that they are limited to single cell in vitro systems.

SUMMARY OF THE INVENTION

Accordingly, one object of the present invention is to provide a widely applicable mechanism for transporting particles, which can comprise or be associated with biological substances, into living cells which mechanism does not depend upon the cell type, size, shape, presence or absence of cell wall, cell number, or cellular environment.

Another object of the present invention is to provide a mechanism for transforming large numbers of cells simultaneously and is not limited to singe cell manipulation.

A further object of the present invention is to provide a mechanism for affecting tissues in situ as well as single cells in vitro.

These and other objects can be achieved by increasing the kinetic energy of particles which can comprise or act as carriers for the biological substance sought to be inserted in cells, and propelling the particles at the cells at a speed whereby the particles penetrate the surface of the cells and become incorporated into the interior of the cells.

Broadly, these objectives can be accomplished by apparatus adapted to accelerate the particles to a predetermined speed and further adapted to propel the particles toward a target, preferably in a directed manner. One such apparatus, which can be referred to as a "gas blast" device, comprises tube means closed at one end and having an outlet at the other end, means for injecting a pressurized gas into said tube means adjacent the closed end thereof, apertured deflector means adjacent the other end of the tube means for deflecting a portion of the pressurized gas to prevent undue damage to the cells, and delivery means communicating with the tube means intermediate the ends thereof for supplying particles into the tube means in a manner adapted to entrain the particles in the pressurized gas passing through the tube means.

Another means for accelerating the particles comprises a macroprojectile containing the particles, means for accelerating the macroprojectile and means for stopping the macroprojectile while allowing the particles to maintain the previously acquired velocity and to be propelled toward a target.

Yet a third means for accelerating the particles to high velocities comprises a high speed rotational device which accelerates to a desired velocity, particles bound or dispersed to its outer perimeter and releases the particles in a manner which propels at least a portion of the particles toward a target. Preferably, the rotational devise is operably associated with a means which releases at least a substantial portion of the particles in a predetermined straight path tangential to the localized point of release.

BRIEF DESCRIPTION OF THE DRAWINGS

FIGS. 1a to 1d show four methods of introducing biological substances into cells by the use of accelerated particles. In 1a, an inert microsphere is coated with a biological substance, accelerated, and after perpetrating the target cell microsphere releases the substance from its surface. In 1b, a target cell is surrounded with a biological substance, and is bombarded with an uncoated inert microsphere which carries the biological substance into the cell in its wake. In 1c, a dried bacterium is employed as a projectile, carrying DNA in its interior, which is released into the target cell after perpetration and bacterial lysis. In 1d, a bacteriophage particle is used as a projectile, carrying DNA in its interior which is released into the target cell after penetration and phage coat breakdown.

FIGS. 3a and 3b show the introduction of four-micrometer diameter tungsten spheres into onion epidermal cells using particle acceleration as depicted in FIG. 2a. FIG. 3a shows the exterior of the cell covered with tungsten spheres following bombardment. FIG. 3b shows tungsten spheres having entered the interior of the same cells (focusing 15 micrometers below the cell surface).

FIG. 4a shows the exterior of the cell covered with tungsten spheres after bombardment. FIG. 4b shows tungsten spheres which have entered the interior of the same cells (focusing 50 micrometers below the cell surface).

FIG. 5a shows a cell (indicated by the arrow) having five tungsten spheres on the surface. FIG. 5b shows the same cell with a focus at about 65 micrometers beneath the cell surface.

FIG. 6a shows 16 tungsten spheres on the surface of the cell. FIG. 6b shows nine tungsten spheres in the interior of the same cell with a focus at about 65 micrometers beneath the cell surface.

DETAILED DESCRIPTION OF THE INVENTION

According to the method of the present invention, particles of the appropriate size, accelerated to appropriate velocities can readily penetrate thin barriers such as cell walls and cell membranes, thereby entering into the cell cytoplasm. In this way, particles such as inert particles coated, impregnated, or otherwise operably associated with biological substances, or frozen or otherwise solid biological particles can be introduced into cells (FIGS. 1a to 1d).

The only physical limitation upon the particles is that they have sufficient mass to acquire the necessary kinetic energy to penetrate the particular cell sought to be penetrated and that they have integrity sufficient to withstand the physical forces inherent in process.

The size of the particles is only broadly critical. Usually the particles have a diameter between about 10 nanometers and about a few micrometers. In order to penetrate the cell and become incorporated into the interior of the cell without killing the cell, the maximum size of the particle must be a size substantially smaller than the cell sought to be penetrated. Small cells e.g. cells with a diameter of about ten micrometers or less usually will only tolerate particles having a diameter about ten times smaller than their own diameter. Larger cells tend to tolerate particles having larger particle diameter. The viability of cells depends in part on the particular cells and the environment of the cell at the time of penetration. Where necessary the maximum size of particle tolerated by a particular cell can be readily determined by accelerating inert particles into cell samples and examining the viability of the resultant cell samples. The minimum size of the particle is governed by the ability to impart sufficient kinetic energy to penetrate the desired cell. Generally, the optimum particle is small enough to produce minimal cell damage and large enough to acquire sufficient momentum to penetrate the cell; momentum being a function of size, density and velocity.

The velocity to which the particles must be accelerated likewise depends on the size and density of the particle, as well as the nature of the physical barriers surrounding the particular cell. The desired velocity is that minimum velocity sufficient to impart the required kinetic energy to cause the particle to penetrate and become incorporated into a desired cell. For onion epidermal cells the velocity required for cell penetration by 4 micrometer tungsten spheres is in the order of about 400 feet per second. The velocity for cells with thinner cell walls or no cell walls will be a function of particle size and density and required penetration depth. As previously stated the particle velocity required for a particular cell in a particular environment can be determined by the use of inert spheres of appropriate size and density, e.g. metal or plastics or mixtures thereof, prior to the use of particles comprising the biological material.

Figure 2A:
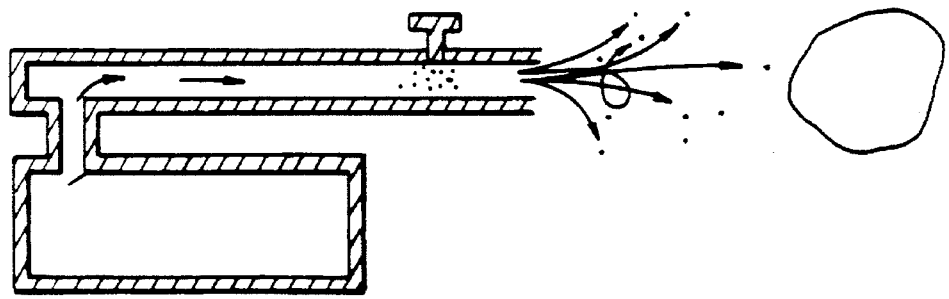
FIGS. 2a to 2e show various mechanisms for acceleration of small particles to high velocity, for the purpose of bombarding cells. In 2a, compressed gas is used to accelerate particles simply and directly. In 2b, a blast-plate is used to translate the kinetic energy of a bullet-sized particle to the small particles on the far side of a plate. This offers potentially higher velocities with less associated air blast. In 2c, a bullet-sized particle is used to accelerate small particles in a forward cavity, and a stopping device is used to stop the larger particle, while allowing the small particles to continue full speed. In 2d, a high-speed rotor is used to accelerate to very high velocities small particles attached or dispersed to its perimeter. When allowed to escape from the rotor, such particles can come off the rotor tangentially at high speed. In 2e, electrostatic acceleration of small charged particles is employed as is used in sub-atomic accelerators.

According to the method of the present invention, the particles can be accelerated by any accelerating means suitable for accelerating small particles. The accelerating means is not critical, provided that the means is capable of providing a plurality of particles to a specific target at a predetermined velocity in a manner which does not adversely effect the biological substance associated with the particle. Examples of such accelerating means include gas blast means (e.g. FIG. 2a), mechanical impulse means (e.g. FIGS. 2b and 2c), centripetal means (e.g. FIG. 2d) and electrostatic means (e.g. FIG. 2e). Within the scope of this invention the method of the invention can be practiced by accelerating means which operate on the above principles or other principles which accomplish the desired result. The structural details of any specific apparatus can vary from these specifically discussed herein as can be perceived by one skilled in the art of acceleration devises.

As set forth above, the particles can be, for example, inert particles, particles coated or impregnated with biological substances, or frozen or otherwise solid biological particles.

Examples of inert particles include ferrite crystals, gold or tungsten spheres, and other metal spheres and particles of high density, for example about 10 to about 20 g/cm$^3$ as well as spheres and particles of low density (for example 1–2 gm/cm$^3$) such as glass, polystyrene, and latex beads.

Biological particles include any biological substance which can be freeze dried, or otherwise prepared as free particles or otherwise used as a particle projectile for cell penetration. Examples of such particles include bacteria, viruses, organelles, and vesicles. Once in the cells, such biological particles or portions thereof would be expected to return to their natural state undamaged (e.g. hydrate, thaw, dissolve, etc.) or otherwise to contribute a desired biological activity within the cell.

Further, according to the present invention, biological substances can be coated on, bonded on or precipitated onto the surface of inert particles such as latex beads, high density metal spheres or ferrite crystals, or the particles can be impregnated with various biological substances. Such coated or impregnated particles can then act as carriers, carrying the biologically active substances into the cell. Once in the aqueous environment of the cytoplasm, the biological substances would dissolve or be dispersed into the cyto-solution (FIG. 1a).

Additionally, the cells can be bathed in or surrounded by a biological solution and bombarded with inert particles to pull into the cell, in the wake of the particles, a given volume of the external biological solution (FIG. 1b). The particles can be uncoated or coated with a biological substance which is the same or different from the biological substance bathing or surrounding the cells. In the same manner, biological particles can be propelled at cells bathed in or surrounded by a biological solution.

Examples of biological substances which can be coated onto or impregnated into inert particles or used to bathe the cell include biological stains such as fluorescent or radiolabeled probes, viruses, organelles, vesicles, proteins such as enzymes or hormones, and nucleic acids such as DNA and RNA.

Such penetration of living cells with small particles projected from a particle accelerator is possible with a minimum of cell handling, cell preparation, or cell disruption. Lesions in the cell membrane need not be much larger than would be achieved using microinjection procedures and need only remain open for a fraction of a second, e.g., the transient time of the particle. Particles can be accelerated in large numbers to affect large numbers of cells simultaneously.

Further, according to the present invention, the cell type, size, shape, presence or absence of cell wall, cell number, or cellular environment is not critical and should not significantly alter effectiveness. Examples of the wide array of cells which can be subjected to this invention include algal cells, bacteria, single cell protozoa, plant pollen, plant protoplasts, animal eggs, animal bone marrow cells, muscle or epidermal cells, or any similar plant or animal cell.

Additionally, since there is spacial separation between the transforming apparatus of the present invention and the recipient cells, the present invention allows for the treatment or modification of cells in tissues in their natural state, i.e., in situ. Examples of tissues which can be bombarded include plant tissue such as meristem tissue, and human tissue or other animal tissue such as epidermal tissue, organ tissue, tumor tissue and the like. It is noted that air-delivered injection devices are currently employed medically to administer vaccines, but the administration is into tissue fluid or blood, and not directly into living cells. Such tissue treatment or modification would require such levels of particle bombardment of a tissue which would not be lethal to tissue, although some cells might die, but which would affect a significant fraction of the cells in that tissue.

Figure 7B:
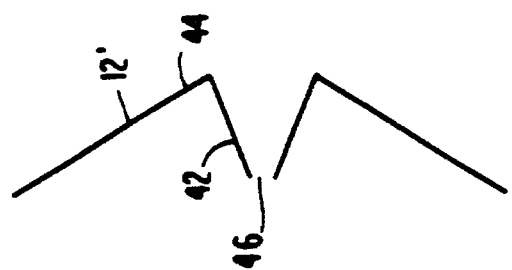
FIG. 7b is a schematic diagram of another embodiment of a deflector.
Figure 7A:
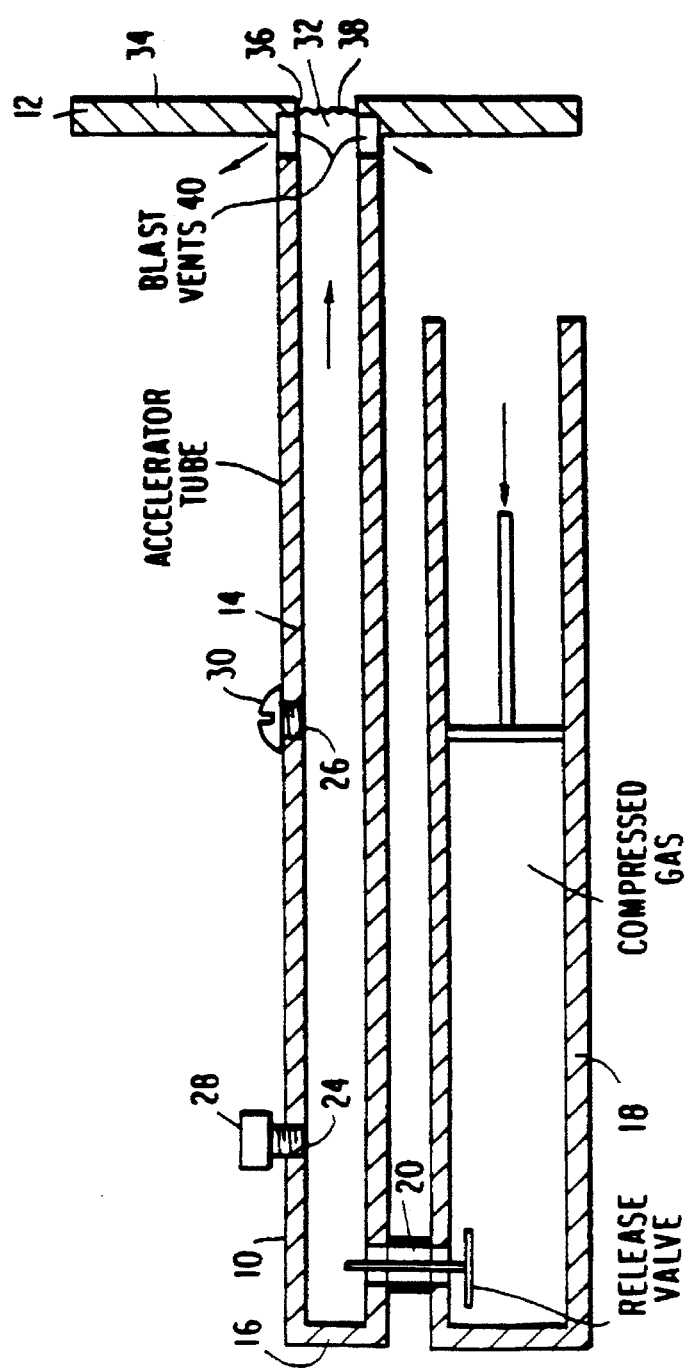
FIGS. 7a is a schematic diagram of a compressed gas accelerator according to the present invention with one embodiment of a deflector.

One embodiment of the apparatus of the present invention is schematically illustrated in FIG. 7a and is basically comprised of a particle accelerator device 10 and a blast deflector 12. The particle accelerator 10 is comprised of an elongated hollow accelerator tube 14 having an end wall 16 closing one end of the tube. A source of compressed gas 18 communicates with the accelerator tube 14 adjacent the closed end thereof by means of the passage 20 which is controlled by a suitable valve means 22 adapted to be selectively controlled by an operator. A pair of particle inlets 24 and 26 are provided in spaced relation to each other along the length of the tube 14. As illustrated in FIG. 7a, a suitable particle supply means 28 is threaded into the inlet 24 adjacent the closed end of the tube and a plug 30, in the form of a screw or the like, is threaded into the inlet 26. Depending upon the nature of the particles involved and the desired acceleration for the particles, the particle supply means and the plug 30 can be reversed in the inlets 24 and 26.

In the operation of the apparatus, the valve 22 is operated for a discrete period of time, thereby allowing a blast of compressed gas to enter into the closed end of the tube 14. As the blast of compressed gas travels along the length of the tube toward the outlet 32, a supply of particles from the particle supply device 28 will be delivered into the gas stream through the inlet 24. The stream of gas carrying the particles will then impinge upon a cell substrate disposed at an appropriate distance from the outlet 32 of the tube 14.

In the event that it is necessary to locate the cell substrate in extremely close proximity to the outlet 32 of the accelerator tube 14, a blast deflector 12 may be provided to prevent undue cell damage. The blast deflector 12, as illustrated in FIG. 7a, is comprised of a plate 34 having an aperture 36 extending therethrough with a reticulated screen 38 secured in the aperture 36. The blast deflector 12 may be fitted over the end of the accelerator tube 14 with the screen 38 aligned with the outlet 32. Suitable exhaust apertures 40 may be provided in the end of the tube 14 adjacent the outlet 32 so that the main blast may be deflected laterally outwardly through the apertures 40 while permitting a small amount of the airstream with the particles entrained therein to pass through the reticulated screen 38 for impingement on the cell substrate.

A modified form of the blast deflector 12' is shown in FIG. 7b and is comprised of two interconnected oppositely directed truncated conical members 42 and 44. The truncated conical member 42 is open at both ends with the smaller diameter opening 46 adapted to be disposed adjacent the outlet 32 of the accelerator tube 14. Any suitable means can be provided for mounting the blast deflector 12' adjacent the end of the accelerator 14. Thus, a small amount of the air stream with the particles entrained therein can pass through the small diameter opening 46, while the main blast is deflected along the outer conical surface of the member 42. The main blast will then impinge upon the conical surface of the oppositely directed member 44 to deflect the blast laterally outwardly and rearwardly away from the cell substrate.

The details of the above particle accelerator and the blast deflector may be varied within the scope of the present invention.

Figures 8A, 8B:
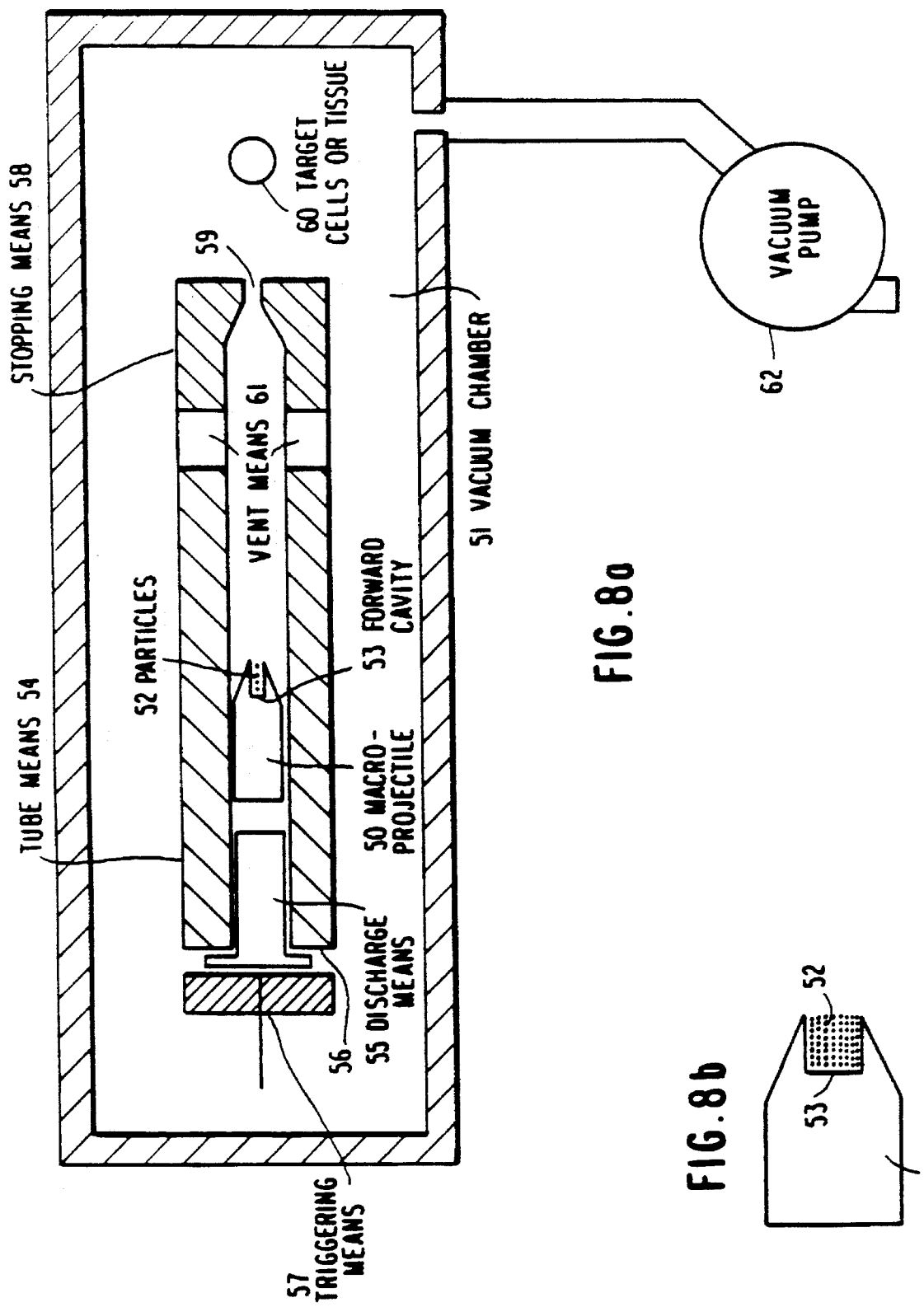
FIG. 8a is a schematic diagram of a accelerator apparatus which accelerates a macroprojectile containing particles and a means for stopping the macroprojectile while allowing the particles to proceed toward a target with a predetermined acquired velocity.
FIG. 8b is a diagram of a macroprojectile containing particles.

Another embodiment of the apparatus of the present invention is illustrated in FIG. 8a and is comprised of a macroprojectile 50 (FIG. 8b), with a forward cavity 53 containing particles 52, contained in tube means 54, which has a discharge means 55, for example an explosive charge or compressed gas source rearward the macroprojectile, e.g. mounted at rear end 56 of the tube means, which discharge means is actuated by a triggering means 57. The forward end of the tube means has a macroprojectile stopping means 58 adapted to stop the accelerated macroprojectile while allowing the particles to continue through a aperture 59, toward a target cell or tissue 60. Vent means, e.g. holes, 61 in the tube means allows dissipation of the accelerating force proximal the forward travel limit of the macroprojectile. To minimize air resistance the entire apparatus and target can be enclosed in a vacuum chamber 51 connected to a vacuum pump 62, to allow the process to be operated at reduced air pressure.

Figure 9:
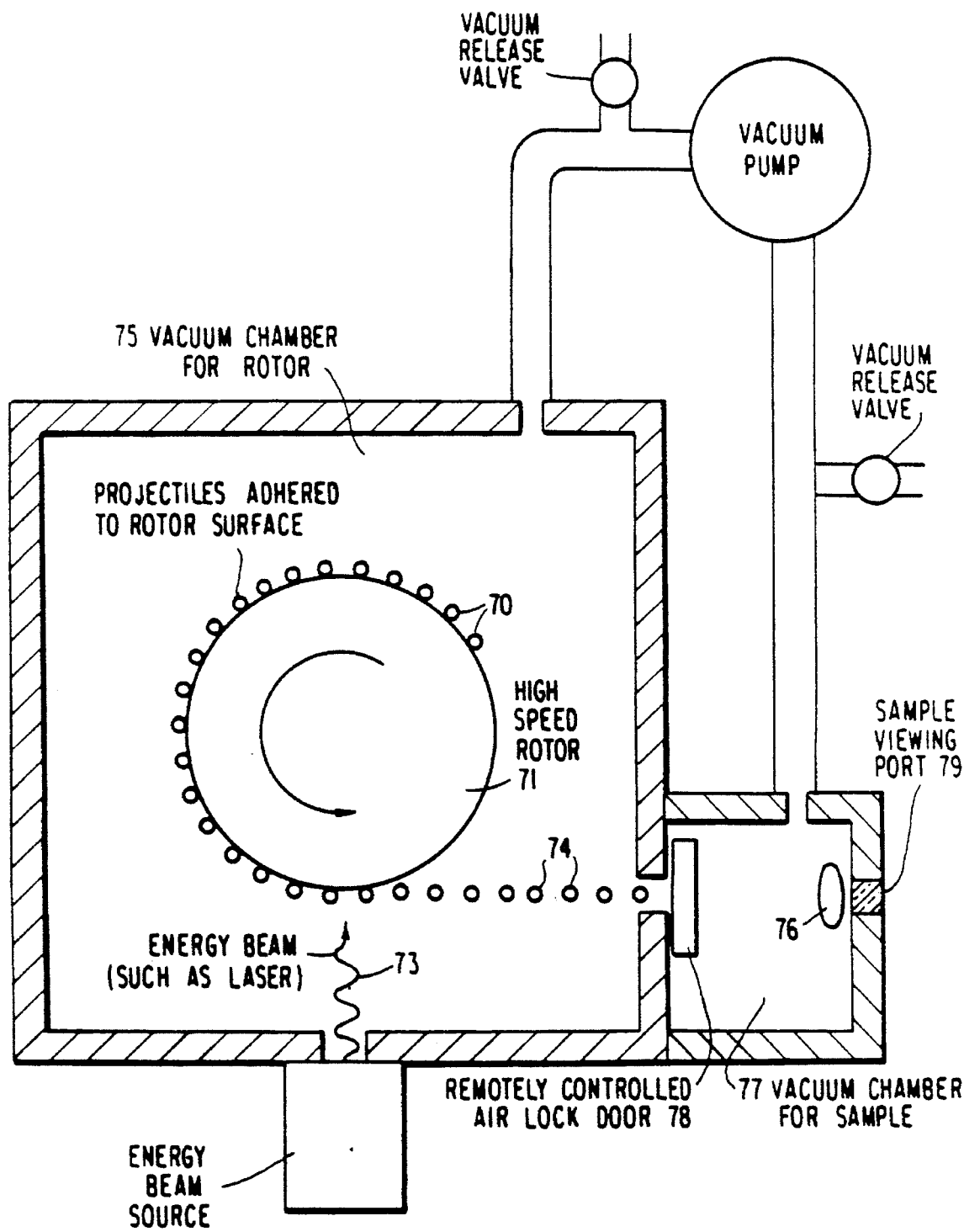
FIG. 9 is a schematic diagram of an accelerator apparatus employing centripetal acceleration. Particles are adhered to the outer surface of a rotational device and the device accelerated to a predetermined speed. The particles are freed from the surface of the rotating device for example by means of a directed energetic beam, e.g. a laser beam, which allows the particles to continue at a predetermined velocity in a straight line tangential to the point of release.

Yet another embodiment of the apparatus of the present invention is illustrated in FIG. 9. Particles 70 are bound or adhered to the outer edge of a rotor 71 and thereby accelerated to a high velocity. The velocity of the particles is controlled by the circular velocity of the rotor. Controlled release of the particles is achieved by focusing an energetic beam 73, such as a laser beam, at a specific point on the outer edge of the rotor. The energy of the beam is adapted to and causes release of particles from the surface of the rotor, causing such particles 74 to continue at a predetermine velocity in a straight line tangential to the point of release and thus to be directed toward a target. This result can optimately be achieved in a vacuum chamber 75 which allows maximal speeds for the rotor and minimal frictional deacceleration of the particles. Preferably, the target cell or tissue 70 is placed in a sample compartment 77, separable from the main vacuum chamber 75 by a moveable airlock door 78 and having independent means for control of the pressure to allow changing of samples without loss of vacuum in the main chamber. This preferred two chamber embodiment also avoids extended sample exposure to hard or sudden vacuum which would result in tissue desiccation. The sample chamber can be fitted with a sample viewing port 79, or alternatively, with a opening surrounding by a sealing means (not shown) to allow the use of a human or animal anatomical portion or a portion of a whole living plant as a target.

It is significant to note that the use of an energetic beam such as a laser beam, ion beam, electron beam to dislodge particles adhered or bound to a rotor means to cause particles to flow in a path tangential to the rotor arc is considered novel. The energy beam is selected to impart energy of a nature and in an amount sufficient to overcome the forces of adhesion existing between the particle and the rotor means and release the particle from the rotor without adversely affecting the particles' essential properties.

An alternative embodiment of the above centripetal device comprises a rotor having one or more passageways from its center to its outer edge adapted to dispense particles from the outer edge of the rotor. In this device particles would be dispensed over a 360° arc. This apparatus would be less efficient with respect to a small target, but on the other hand would allow the use of multiple or larger area targets mounted on the inside wall of an enclosure surrounding the rotor.

As is clear from the above detailed description of the present invention, the nature of the accelerated particle or "particle gun" approach is such that it should be a suitable substitute for any existing intracellular delivery system. The potential applications are extremely diverse. Moreover, a particle accelerator has the new and novel capability to transform general tissues in situ. This new and novel capability gives rise to new and novel potential applications of the technology, not possible with any other technology. Two important new applications of particle accelerator mediated in situ tissue transformation are considered to be: (1) germline transformation of plants, and (2) human gene therapy. These new applications are demonstrated below and are illustrative only and not intended to limit the present invention.

Germline Transformation of Plants—Most plant species cannot currently be regenerated from protoplasts. Even in those species which can be regenerated, the time and expense involved in regeneration represent significant obstacles. There has been considerable effort devoted to the problem of regeneration in many plant species, often without success. To continue to try to develop reliable regeneration procedures for each crop plant will be very expensive, and in many cases prove impractical or impossible. These problems can be completely circumvented by using germline cells instead of plant protoplasts, as targets for genetic manipulation.

The two logical targets for plant germline transformation are pollen and meristem domes. Transformation of pollen is the method of choice for sexually-propagated crops, such as grain crops while transformation of meristematic domes is the method of choice for asexually-propogated crops such as most fruits, potato, sugar cane, etc. Either approach would be expected to directly produce transformed whole plants.

While it is conceivable that plant pollen can be effectively microinjected, particle bombardment would be much more effective, since thousands of pollen cells could be treated simultaneously. Meristem transformation could only be achieved by particle bombardment as described below.

The meristematic dome can be exposed surgically, as is commonly done for meristem culturing and then bombarded with DNA-carrying particles. Exposure times could be increased up to a near-lethal level, as determined emperically. At this point a large number of meristematic cells can be transformed. Treated meristems are then allowed to grow out into chimeric shoots, from which stable transformed sectors are selected.

Somatic Human Gene Therapy—The potential significance of human gene therapy has been recognized for quite some time (*The Prospects of Gene Therapy*, 1971, Fogarty International Center Conference Report, Fresse E. (ed.), DHEW Publ. No. (NIH 72-61)), although this has not been a particularly active area of research for lack of effective means of incorporating genes into human tissues. Over 1500 human diseases are known to be genetically determined (McKusick, V. A., 1971, *Mendelian Inheritance in Man*, John Hopkins Press, Baltimore). There are at least 92 human disorders for which a single enzyme deficiency is the cause, i.e., based upon a single gene defect (McKusick, V. A., 1970, *Ann. Rev. Genet.*, 4:1). When genetic disease is associated with an enzyme deficiency in a specific tissue, particle gun bombardment can be used to introduce therapeutic genes.

For example, a patient with sickle cell anemia can have bone marrow tissues bombarded with particles carrying the appropriate DNA, i.e. inserting sequences expressing functional $Hb^a$ gene, to restore normal function to those tissues, producing a sufficient number of normal red blood cells to produce a healthy individual.

Healthy tissues can likewise be subjected to particle bombardment therapy, where significant improvements might be made. Disease-resistance conferring genes might potentially be engineered for example, by using parasite-derived resistance as described by Sanford and Johnston (in press). Alternatively, health-promoting biosynthetic capabilities might be introduced in human tissues, such as ability to synthesize vitamins, or new anticancer compounds (Ames, B. N., 1983, "Dietary Carcinogens and Anticarcinogens", *Science*, 221:1256–1264).

While the emphasis herein has been placed on the use of the particles to add biological material to a cell, it should be noted that the insertion of biological inert particles into cells is within the scope of the invention and has utility. The particles can be used, for example, as cell markers and the like.

The present invention will now be described by reference to specific examples which are meant to be illustrative only and are not intended to limit the invention.

EXAMPLE 1

Demonstration Of Penetration Of Cell By Metal Spheres Accelerated By Gas Blast Apparatus Onion epidermal cells were bombarded with tungsten spheres one and four micrometer in diameter, which had been accelerated to a high velocity using an air blast generated by the apparatus described above. The outer scales of a mature onion were removed to expose younger scales. The expressed epidermis of such inner scales were bombarded with no further preparation. The distance between the particle accelerator and the epidermal cells varied from 1 cm to 20 cm, with greater distance yielding less cellular disruption, but lower percent penetration. The exit velocity of the air blast from the accelerator was estimated to be below about 600 feet per second.

Both the one-micrometer and four-micrometer spheres entered into the onion epidermal cells without any gross damage resulting to the surface of the epidermal cells.

A fraction (about 5%) of the one-micron tungsten spheres penetrated the onion epidermal cells. To achieve a higher rate of penetration with smaller particles, a higher velocity can be used.

Results of the bombardment with four-micrometer spheres are shown in FIGS. 3a, 3b, 4a, 4b, 5a, 5b, 6a, and 6b. As can be seen from the figures, four-micrometer spheres entered into onion epidermal cells in significant numbers. Rates of particle penetration in some cases approached 50% of the spheres employed. Further, large numbers of cells were simultaneously penetrated, often with multiple particles. The results also indicate that accelerated tungsten spheres penetrate as deeply as three cell layers.

Figure 3A:
Figure 3B:
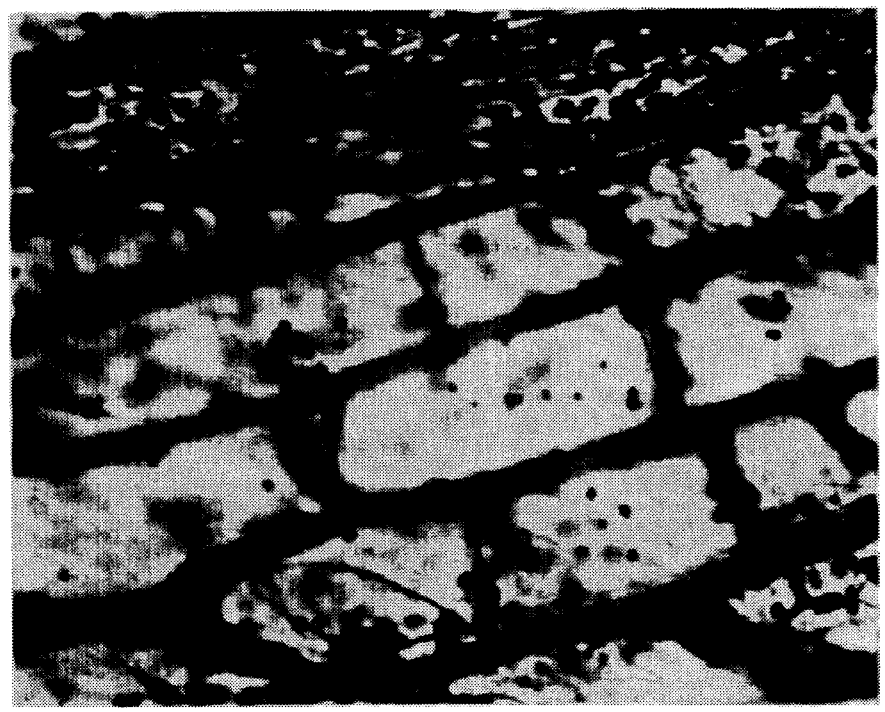

As can be seen from FIG. 3b (focusing 15 micrometers below the cell surface), four-micrometer diameter tungsten spheres penetrated the cell membrane and entered the interior of the cell with no obvious or gross lesions appearing on the cell surface.

Figure 4A:
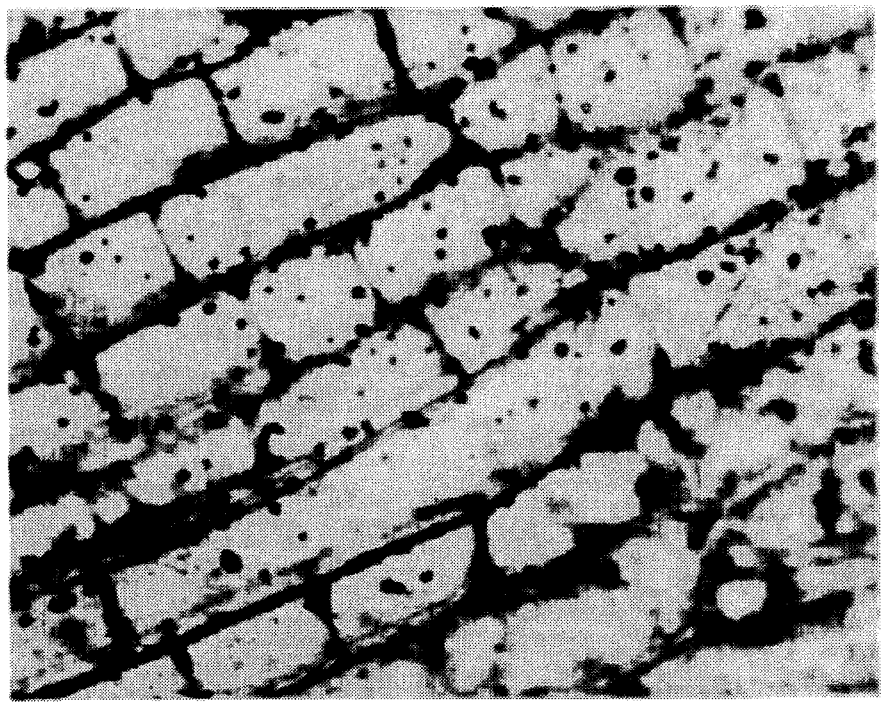
FIGS. 4a and 4b show the introduction of four-micrometer diameter tungsten spheres into onion epidermal cells using particle acceleration.
Figure 4B:

FIG. 4b shows four-micrometer diameter tungsten spheres introduced into onion epidermal cells (at a focus of 50 micrometers below the cell surface). The sphere in the center (arrow) created a star-shaped depression on the far-side envelope of the cell, indicating that the particle still had measurable momentum after passing into the cell.

Figure 5A:
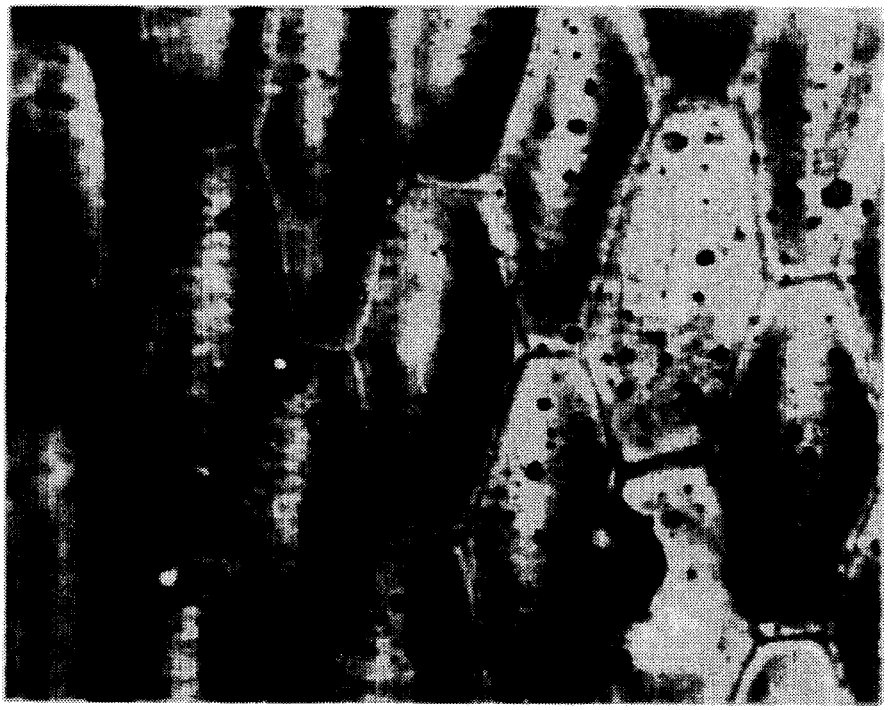
FIGS. 5a and 5b show onion epidermal cells after bombardment with four-micrometer diameter tungsten spheres travelling at velocities of a few hundred feet per second.
Figure 5B:
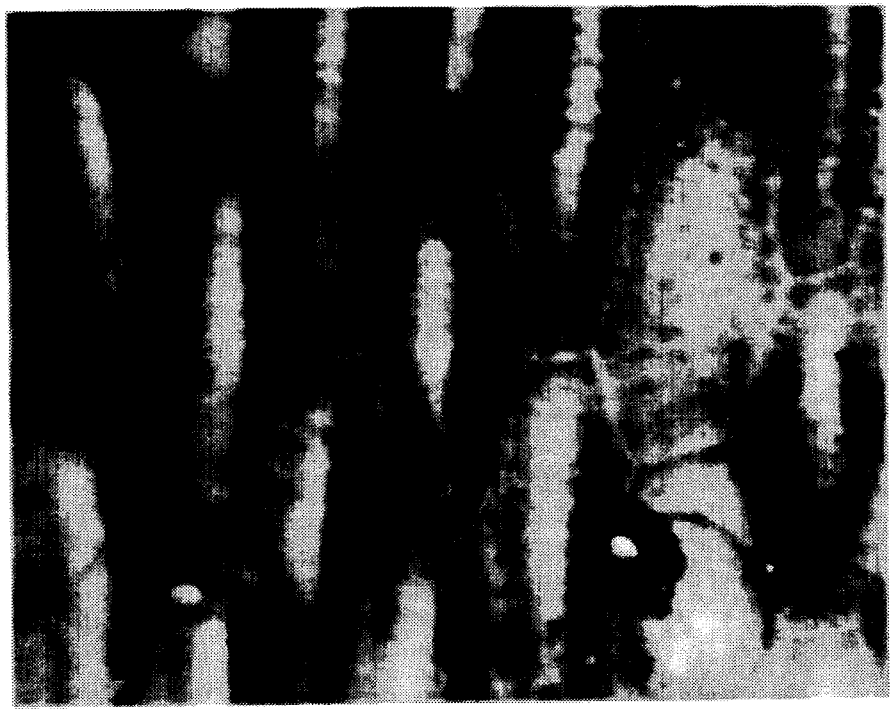

FIGS. 5a and 5b show onion epidermal cells which have been bombarded with four-micrometer diameter tungsten spheres travelling at velocities of a few hundred feet per second. FIG. 5b shows spheres in the interior of the cell (at a focus of about 65 micrometers beneath the surface of the cell). As can be seen, there was no apparent cell disruption.

Figure 6A:
FIGS. 6a and 6b show onion epidermal cells after bombardment with four-micrometer diameter tungsten spheres travelling at velocities of a few hundred feet per second.
Figure 6B:
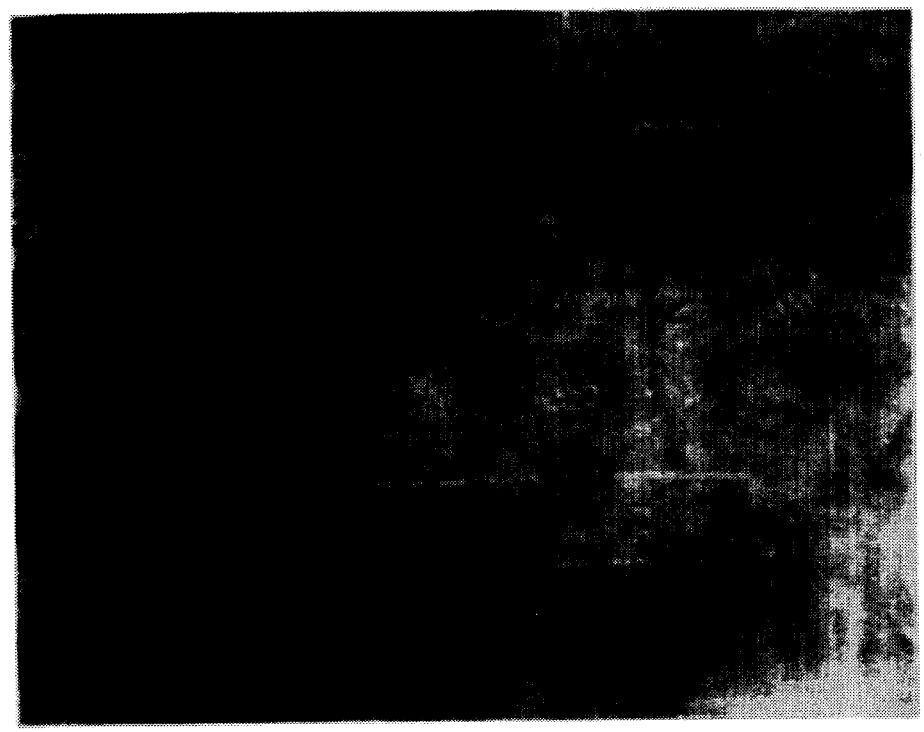

FIGS. 6a and 6b also show onion epidermal cells after bombardment with four-micrometer diameter tungsten spheres travelling at velocities of a few hundred feet per second, but at a higher magnification than shown in FIGS. 5a and 5b (4-micrometer spheres give scale). As can be seen from FIG. 6b nine tungsten spheres entered the interior of the cell (focus was at about 65 micrometers beneath the surface of the cell). Again, no apparent cell disruption was observed.

EXAMPLE 2

Demonstration Of Cell Viability After Penetration By Metal Spheres

Onion epidermal cells were evaluated relative to their viability following bombardment with four-micrometer tungsten spheres, using the conditions of bombardment set forth in Example 1. Although the air blast killed many of the surface cells, a significant number of cells remained alive as determined by microscopic observation of cytoplasm streaming. The number of cells killed was largely a function of the distance of the cells from the accelerator device. The cells containing tungsten spheres had very active cytoplasmic streaming, both one hour after bombardment and 20 hours after bombardment. In some cases, a tungsten sphere could be seen carried along within the cell by the cytostreaming.

EXAMPLE 3

Demonstration Of Mechanical Impulse Acceleration Of Particles

Figure 2B:
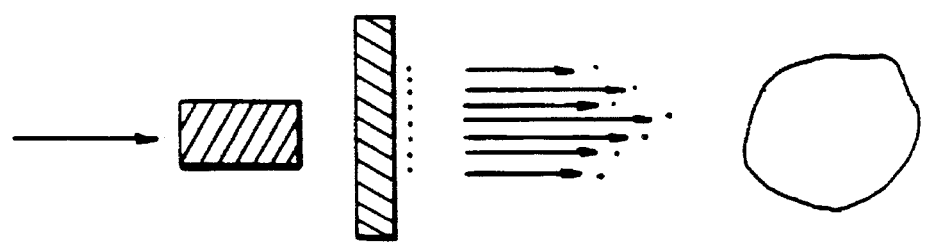
Figure 2C:
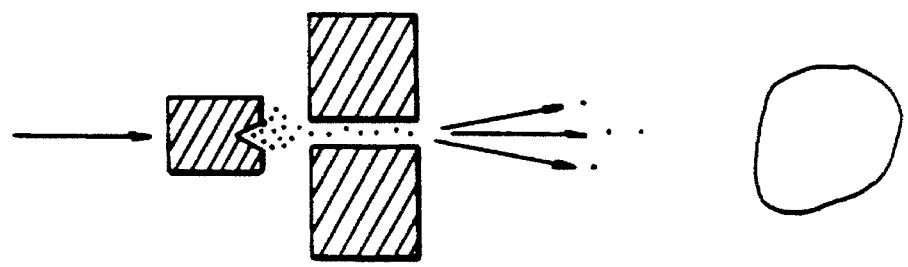

This method for accelerating small particles is based upon the concept of mounting the small particles on a larger particle or surface, accelerating the larger body by impact or ballistic means, and then stopping the larger body, while allowing the smaller particles to maintain their velocity (see FIGS. 2b and 2c). With reference to FIG. 2b, a high mass projectile (a lead pellet) was accelerated to approximately 600 feet per second by conventional means (a commercial pellet gun). This was used to impact against a 0.8 mm thick copper plate. Adhering to the reverse side of the plate were 4-micrometer tungsten spheres. As the plate was deformed by the impact, the spheres were accelerated to a velocity similar to that of the lead pellet, and when the copper plate reached the limit of its deformation, the tungsten spheres separated from its surface and continued at high velocity— penetrating onion epidermal cells in a manner very similar to that observed using air blast acceleration. The area of effective penetration was smaller than using an air blast, being limited to the area immediately below the pellet's point of impact on the copper plate. This method is desirable in that higher velocities than with an air blast should be attainable, and in the absence of the potentially damaging air blast. A modification of this principle is represented in FIG. 2c. A scale up design of an apparatus employing this principle is illustrated in FIG. 8a.

EXAMPLE 4

Demonstration Of Centripetal Acceleration Of Particles

Figure 2D:
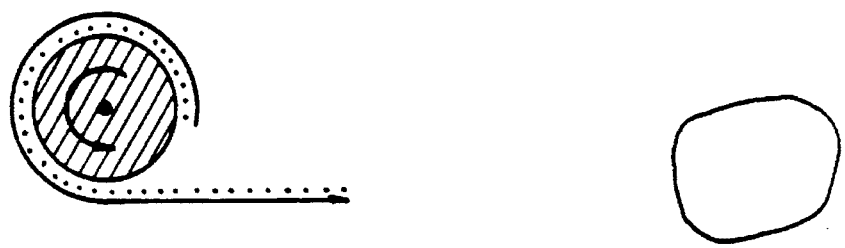
Figure 2E:
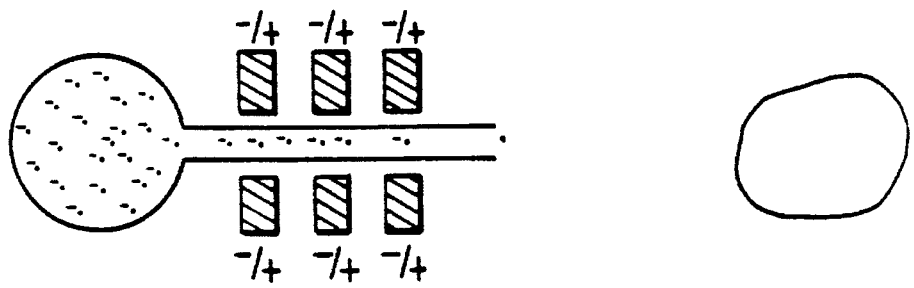

This method exploits the high velocities generated on the perimeter of a high speed rotor, for the purpose of accelerating small particles (FIG. 2d). Using ultracentrifuge technologies, outer perimeter velocities on rotors can reach several thousand feet per second. Particles could be delivered to the outside of the rotor by a variety of mechanisms, including channels radiating from the center of the rotor, or by a stream of particles to be caught by external ridges on the outer surface of rotor.

Figure 10:
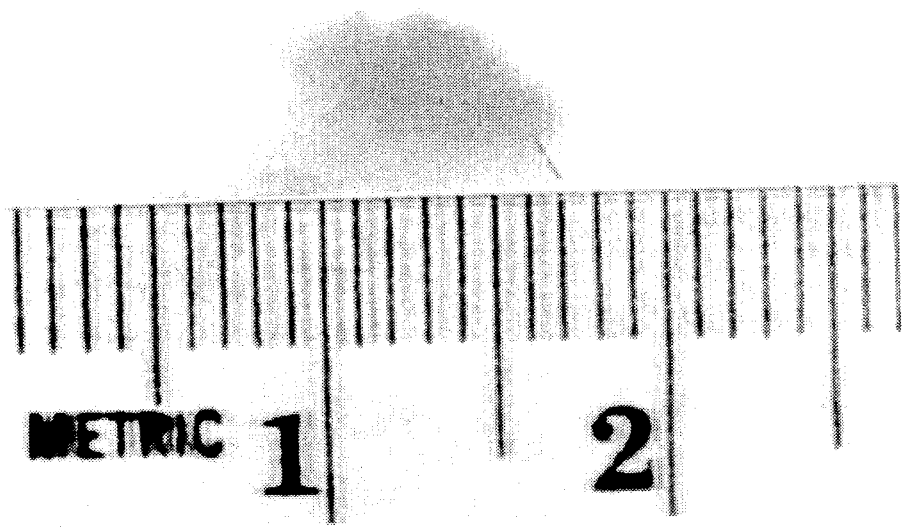
FIG. 10 is a photograph of the pattern of tungsten spheres as released from a high speed rotational device by a YAG laser beam, as collected on Scotch tape 3 inches from the point of release. The actual beam is round, but the pattern on the tape is oblong because the tape was at a 45° angle to the particle beam.
Figure 11:
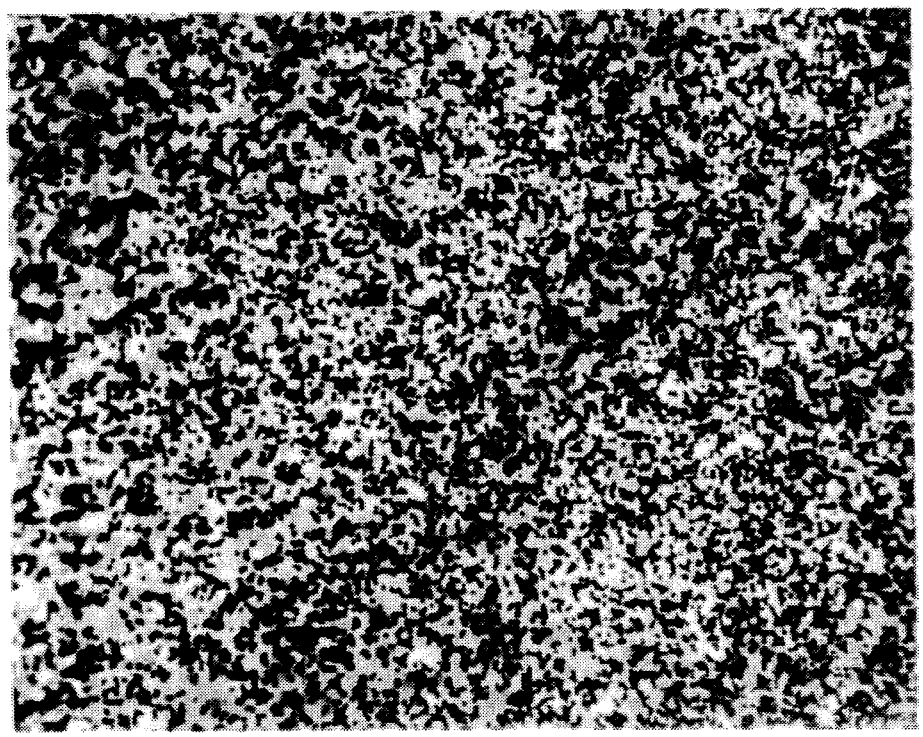
FIG. 11 is a microphotograph of the same pattern of tungsten spheres as in FIG. 10, showing the absence of clumping and the uniform dispersion of the particles.

With reference to FIG. 9, four micrometer tungsten spheres were adhered to the rotor of an Eppindorff microcentrofuge by applying the particles as an ethanol suspension, followed by drying. A pulsed YAG laser was focused on the surface of the spinning rotor, such that particles were released from the surface of the rotor and flew tangentially from the point of laser contact. The particles were collected on Scotch tape, to determine the width of the resulting particle beam. In spite of high air turbulence (no vacuum was employed), the beam was relatively tightly focused, being only 2 and 3 times the width of the laser beam (3 mm), 3 inches from the point of release (see FIG. 10). The pattern of distribution within the particle beam was examined microscopically, and was found to be extremely uniform with no clumping (FIG. 11). The rotor had a circumference of 22 inches and a speed greater than 12,000 rounds per minute, giving the particles a velocity greater than 366 feet per second. The YAG laser was used at a frequency of 10 pulses per second. Wavelengths of 532 nm and 1.06 um were both found to be effective in releasing the particles, when used in the energy range of 15–30 millijoules.

Particles have been similarly attached to an ultracentrifuge rotor and have been brought us to velocities as high as 1,600 feet per second, greatly exceeding those velocities found to be effective for cell penetration using the two previous methods described above. This apparatus is capable of delivering particles over a wide range of speeds.

While the invention has been described in detail and with reference to specific embodiments thereof, it will be apparent to one skilled in the art that various changes and modifications can be made therein without departing from the spirit and scope thereof.

We claim:

1. An apparatus for injecting particles into cells wherein said apparatus accelerates particles having a diameter sufficiently small to penetrate and to be retained in preselected target cells toward said target cells, to thereby cause said particles to penetrate said cells and become incorporated into the interior of said cells, said apparatus comprising tube means closed at one end and having an outlet at the other end, means for injecting a pressurized gas into said tube means adjacent the closed end thereof, a source of said particles, and delivery means communicating with the said tube means intermediate the ends thereof for supplying particles from said source into the pressurized gas passing through said tube means.

2. An apparatus as set forth in claim 1, further comprising apertured deflector means adjacent the other end of said tube means for deflecting a portion of the pressurized gas to prevent undue damage to said cells, said deflector means being comprised of a substantially conical member having an aperture in the apex thereof adjacent said other end of said tube means and an oppositely directed truncated conical member secured to the larger diameter end of said first mentioned conical member for directing a portion of the pressurized gas in the opposite direction while allowing a portion of the pressurized gas with entrained particles to pass through said aperture.

* * * * *